(12) United States Patent
Chuang

(10) Patent No.: US 7,015,304 B1
(45) Date of Patent: Mar. 21, 2006

(54) SOLVENT FREE LOW-MELT VISCOSITY IMIDE OLIGOMERS AND THERMOSETTING POLYIMIDE COMPOSITES

(75) Inventor: Chun-Hua Chuang, Brecksville, OH (US)

(73) Assignee: The United States of America as represented by the Administrator of the National Aeronautics and Space Administration, Washington, DC (US)

( * ) Notice: Subject to any disclaimer, the term of this patent is extended or adjusted under 35 U.S.C. 154(b) by 0 days.

(21) Appl. No.: 10/897,279

(22) Filed: Jul. 23, 2004

(51) Int. Cl.
*C08G 73/10* (2006.01)
*C08G 69/28* (2006.01)
*C08G 69/26* (2006.01)
*B32B 27/00* (2006.01)

(52) U.S. Cl. ...................... 528/353; 528/125; 528/126; 528/128; 528/172; 528/173; 528/176; 528/179; 528/185; 528/188; 528/220; 528/229; 528/350; 428/411.1; 428/473.5; 428/395; 264/45.1; 264/46.4; 264/510; 264/516

(58) Field of Classification Search ................ 528/353, 528/350, 125, 126, 128, 172–173, 176, 179, 528/185, 188, 220, 229; 428/411.1, 473.5, 428/395, 220; 264/46.1, 46.4, 510, 516
See application file for complete search history.

(56) References Cited

U.S. PATENT DOCUMENTS

| | | | | |
|---|---|---|---|---|
| 5,138,028 A | | 8/1992 | Paul et al. ................. 528/353 |
| 5,322,924 A | * | 6/1994 | Chuang et al. ............. 528/353 |
| 5,939,521 A | * | 8/1999 | Chuang ..................... 528/353 |
| 6,069,278 A | * | 5/2000 | Chuang ..................... 564/418 |
| 6,136,949 A | * | 10/2000 | Earls et al. ................. 528/353 |
| 6,281,323 B1 | * | 8/2001 | Yokota et al. .............. 528/170 |
| 6,359,107 B1 | | 3/2002 | Connell et al. ............. 528/353 |
| 6,476,182 B1 | | 11/2002 | Auman et al. .............. 528/353 |
| 6,784,276 B1 | * | 8/2004 | Chuang ..................... 528/170 |

* cited by examiner

Primary Examiner—P. Hampton Hightower
(74) Attorney, Agent, or Firm—Kent N. Stone; James V. Tura

(57) ABSTRACT

This invention relates to the composition and a solvent-free process for preparing novel imide oligomers and polymers specifically formulated with effective amounts of a dianhydride such as 2,3,3',4-biphenyltetra carboxylic dianydride (a-BPDA), at least one aromatic diamine and an endcapped of 4-phenylethynylphthalic anhydride (PEPA) or nadic anhydride to produce imide oligomers that possess a low-melt viscosity of 1–60 poise at 260–280° C. When the imide oligomer melt is cured at about 371° C. in a press or autoclave under 100–500 psi, the melt resulted in a thermoset polyimide having a glass transition temperature ($T_g$) equal to and above 310° C. A novel feature of this process is that the monomers; namely the dianhydrides, diamines and the endcaps, are melt processable to form imide oligomers at temperatures ranging between 232–280° C. (450–535° F.) without any solvent. These low-melt imide oligomers can be easily processed by resin transfer molding (RTM), vacuum-assisted resin transfer molding (VARTM) or the resin infusion process with fiber preforms e.g. carbon, glass or quartz preforms to produce polyimide matrix composites with 288–343° C. (550–650° F.) high temperature performance capability.

20 Claims, No Drawings

SOLVENT FREE LOW-MELT VISCOSITY IMIDE OLIGOMERS AND THERMOSETTING POLYIMIDE COMPOSITES

ORIGIN OF THE INVENTION

The invention described herein was made by an employee of the United States Government and may be manufactured and used by or for the Government for governmental purposes without the payment of any royalties thereon or therefor.

FIELD OF THE INVENTION

The present invention is directed to low-melt imide oligomers and thermoset polyimides and to a novel melt process which comprises reacting specific aromatic dianhydrides and aromatic diamines containing one or two benzene rings with a reactive monofunctional endcap such as phenylethynyl phthalic anhydride (PEPA). These reactants are capable of adapting to a melt process at 232–280° C. to produce imide oligomers that have a low-melt viscosity of 1–60 poise at 260–280° C. Due to their low viscosities, these imide oligomers are amenable to low-cost resin transfer molding, vacuum assisted resin transfer molding and resin infusion processes. These oligomers can be cured at 371° C. (700° F.) to produce thermoset polyimide resins having a high glass transition temperature ($T_g$) between 310–380° C. with a 288–343° C. (550–650° F.) high temperature performance capability for aerospace applications and the like. These low-melt oligomers also can be formulated into melt adhesives, composites, and moldings for various other high temperature applications.

BACKGROUND OF THE INVENTION

Polyimides comprise polymers characterized by excellent thermal stability, solvent resistance and high glass transition temperatures ($T_g$). For example, in structural applications, the fiber-reinforced high-temperature polyimide matrix composites offer significant advantages over metals because of their low density and high specific strength. These composites are particularly attractive for use in aerospace systems, e.g. aircraft engines, airframe, missiles, and rockets, where weight is critical. Weight reduction has substantial benefits in terms of fuel savings, increased cargo load, or increased speed and maneuverability. The durability and reliability of the type of polymers used in aerospace components is a critical concern. The polymer requirements for these applications include high glass transition temperatures, ($T_g$), high thermo-oxidative stability and good mechanical properties over a wide range of temperatures. In general, the stability of most polymers are limited to 50° C. lower than their glass transition temperature ($T_g$).

The prior art describes polyimides end-capped with diaryl substituted acetylene by dissolving the monomers, i.e. the dianhydride, diamine and the endcap in organic solvents such as N,N-dimethylformamide or N-methyl-2pyrrolidinone (NMP) and subsequently imidizing the oligomers through heating. The oligomers are isolated by precipitation of the imide solution in water. In the 48th SAMPE Symposium, 1076–1086 (2003), the imide oligomer was prepared by dissolving 2,3,3',4'-biphenyl dianhydride (a-BPDA) together with two diamines and 4-phenylethynylphthalic anhydride in NMP and subsequently imidizing the oligomer by precipitating the slurry in water. The imide oligomers based on a-BPDA, were cured at 371° C. for 1 hour to form polyimides having $T_g$'s equal to 330° C.

The problem that arises from this process is that NMP or any other organic solvent is very difficult to remove from the oligomers. Even when the imide oligomer was recovered by precipitation from the water, traces of NMP were still present. The presence of trace amounts of NMP or any other solvent during the curing or resin transfer molding process (RTM), for example, often creates voids or causes delamination in the final composites. To remove the last trace of solvent, extensive drying under vacuum or passing nitrogen gas in a convection oven are often needed. These extensive measures generally cost additional time and labor which is not very cost effective.

One of the objects of this invention is to produce low-melt viscosity imide oligomers with a reactive endcap to form thermoset polyimide resins by a melt process free of any solvent in order to reduce the manufacturing cost due to the solvent removal process. The oligomers can be cured via the reactive endcap to form thermoset polyimide resins. Accordingly, through the selection of specific diamines together with certain dianhydrides such as 2,3,3',4'-biphenyl dianhydride (a-BPDA) and phenylethynylphthalic anyhdride as the endcap, this invention produces novel imide oligomers capable of achieving low-melt viscosities of 1–60 poises. Upon curing these oligomers at 371° C. (700° F.), the imide oligomers yield thermoset polyimide resins having high glass transition temperatures ($T_g$) equal to or greater than 330° C. These oligomers are adaptable to the RTM, VARTM or resin infusion processes and also can be formulated into adhesives capable of high temperature applications between 288–343° C. (550–650° F.).

The significant advantages of melt processing in accordance with the present invention includes processing the oligomers without the use of solvent such that costly solvent recycling is unnecessary and can be eliminated. High thermal stability is not only essential for processing the melt at temperature greater than or equal to 350° C., but is required also for polyimides for use in various other high temperature applications.

Moreover, the thermosetting polyimides of this invention are easier to process in comparison to other polymers such as the thermoplastic resins in that they have a lower molecular weight and lower viscosities. The thermosetting polyimides' have superior processability in addition to their high temperature capabilities which make them more attractive for use as high performance matrix resins in preparing lightweight, fiber-reinforced polymer matrix composites. These polymer matrix composites are finding increased use in the electronics, automobile and aerospace industries.

SUMMARY OF THE INVENTION

This invention relates to the composition and process for preparing solvent free polyimide thermoset polyimide resins specifically formulated with dianhydrides including 2,3,3',4'-biphenyltetracarboxylic dianydride (a-BPDA), 2,3,3',4-benzophenone dianhydride (a-BTDA), 3,4'-methylene diphthalic anhydride or 3,4'-oxydiphthalic anhydride and a specific group of aromatic diamines endcapped with 4-phenylethynylphthalic anhydride (PEPA) or nadic anhydride.

This invention further relates to a solvent-free process for preparing imide oligomers that have a low-melt viscosity (1–60 poise) at 260–280° C. When the imide oligomer melt was cured at 371° C. in a press or autoclave under 100–500 psi pressure, the oligomer melt resulted in a thermoset polyimide having a glass transition temperature between 310–380° C.

Accordingly, it is an object of this invention to provide thermosetting polyimides derived from the reaction of low-melt viscosity imide oligomers by a melt process without the use of solvents.

It is another object of this invention to provide low-melt imide oligomers cured by resin transfer molding or resin film infusion at temperatures ranging up to about 370° C. (700° F.) to obtain polyimide composites having $T_g$'s of 310° C. and above.

It is a further object of this invention to provide a solvent-free melt process for the preparation of low-melt viscosity oligomers and thermosetting polyimides.

These and other objects of this invention will become apparent from a further and more detailed description of the process as follows.

DETAILED DESCRIPTION OF THE PREFERRED EMBODIMENTS

This invention relates to solvent-free, low-melt imide oligomers and thermosetting polyimides, and to the process of preparing said oligomers and polyimides. More specifically, the invention relate to the process of preparing solvent-free, low-melt viscosity imide oligomers derived from the reaction of effective amounts (sufficient to form the imide) of at least one dianhydride having a formula selected from the group consisting of:

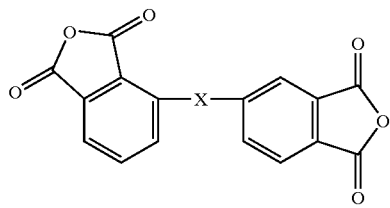

ASYMMETRIC DIANHYDRIDE and

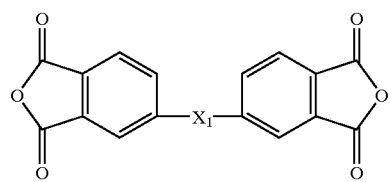

SYMMETRIC DIANHYDRIDE wherein X is selected from the group consisting of nil, C=O, —CH$_2$— and oxygen and X$_1$ is selected from the group consisting of nil, C(CF$_3$)$_2$, CH$_2$— and oxygen, and at least one diamine having a formula selected from the group consisting of:

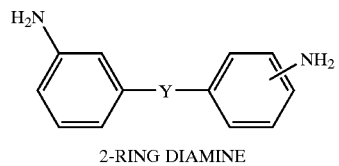

2-RING DIAMINE and

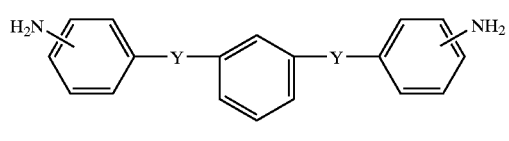

3-RING DIAMINE wherein the Y's are the same or different and are selected from the group consisting of nil, CH$_2$, C$_2$H$_4$, C=O, and oxygen, and the reactive endcap is selected from the group consisting of 4-phenylethynylphthalic anhydride (PEPA) and cis-5-norbornene-endo-2,3-dicarboxylic anhydride (nadic anhydride).

In the reaction, an effective amount is not limited to the reaction of stoichiometric equivalents of all the amine functional groups with anhydride groups from the dianhydride and monofunctional anhydride. It can also include a formulation with up to overall 50% excess of anhydride functional groups derived from 4-phenylethynylphthalic anhydride over all the amine functional groups (Example IV). Furthermore, additives such as 4-phenylethynyldiphenylacetylene or diphenylacetylene can be added over the stoichimometric equivalents of the amine and anhydride (Example V) to increase the glass transition temperature and thermo-oxidation of the thermoset polyimide resins.

The following examples illustrate the novel process and products obtained by specifically reacting these dianhydrides, diamines and 4-phenylethynylphthalic anhydride or nadic anhydride in a solvent-free, melt process to obtain low-melt viscosity oligomers which are subsequently cured to form thermosetting polyimides.

EXAMPLE I 4-phenylethynylphthalic anhydride (6.206 g, 25 mmol) and 2,3,3',4'-diphenyl tetracarboxylic dianhydride (3.678 g, 12.5 mmol) were mixed with 3,4'-diaminobenzophenone (5.5 g, 25 mmol) as a solid mixture with either ball mill or an efficient mechanical stirrer until it became a homogeneous powder mixture. The solid powder mixture was heated to 232° C. (450° F.) from room temperature in 30 minutes and then held at 450° F. for 1 hour to melt the monomers initially and then reacted with all the monomers to form an imide oligomer. The resulting oligomer resin was then grounded into a solid powder with a melt viscosity of 5–10 poises as measured by the Brookfield viscometer. The low-melt viscosity resin was processed by resin transfer molding (RTM) or resin film infusion (RFI) and cured at 700° F. (371° C.) for 2 hours to yield a thermosetting polyimide with a $T_g$ of 350° C.

EXAMPLE II 4-phenylethynylphthalic anhydride (0.24 g, 30 mmol) and 2,3,3',4'-diphenyl tetracarboxylic dianhydride (8.816 g, 30 mmol) were mixed with 3,3'-diaminodiphenylmethane (4.01 g, 45 mmol) as a solid mixture with either ball mill or an efficient mechanical stirrer until it became a homogeneous powder mixture. The solid powder mixture was heated to 232° C. (450° F.) from room temperature in 30 minutes and then held at 450° F. for 1 hour to melt the monomers initially and then reacted with all the monomers to form an imide oligomer. The resulting oligomer resin was then grounded into a solid powder with a melt viscosity of 10–20 poises as measured by the Brookfield viscometer. The low-melt viscosity resin was processed by resin transfer molding (RTM) or resin film infusion (RFI) with a carbon fiber preform and cured at 700° F. (371° C.) for 2 hours with the carbon fiber and then further post cured at 650–700° F. for 8–16 hours to yield a thermosetting composite with a $T_g$ of 310° C.

EXAMPLE III 4-phenylethynylphthalic anhydride (7.44 g, 30 mmol) and 4,4'-(hexafluoroisopropylident)diphthalic anhydride (6.66 g, 15 mmol) were mixed with 1,3-bis(4-aminophenoxy)benzene (30 mmol) as a solid mixture with either ball mill or an efficient mechanical stirrer until it became a homogeneous powder mixture. The solid powder mixture was heated to 232° C. (450° F.) from room temperature in 30 minutes and then held at 450° F. for 1 hour to melt the monomers initially and then reacted with all the monomers to form an imide oligomer. The resulting oligomer resin was then grounded into a solid powder with a melt viscosity of 10–20 poises as measured by the Brookfield viscometer. The low-melt viscosity resin was processed by resin transfer molding (RTM) and resin film infusion (RFI) with a carbon fiber preform and cured at 700° F. (371° C.) for 2 hours with the carbon fiber and then further post curred at 650–700° F. for 8–16 hours to yield a thermosetting polyimide composite with a $T_g$ of 320° C.

EXAMPLE IV 2,3,3',4'-biphenyl tetracarboxylic dianhydride (1.47 g, 5 mmol and 3,3'-diaminobenzophenone (2.1275 g, 10 mmol) were mixed with 20% excess of 4-phenylethynylphthatic anhydride (2.987 g, 12 mmol) as a solid mixture with either ball mill or an efficient mechanical stirrer until it became a homogeneous powder mixture. The solid powder mixture was heated to 232° C. (450° F.) from room temperature in 30 minutes and then held at 450° F. for 1 hour to melt the monomers initially and then reacted with all the monomers to form an imide oligomer. The resulting oligomer resin was then grounded into a solid powder for resin transfer molding (RTM) or resin infusion (RFI) processes and cured at 700° F. (371° C.). The polyimide resin or composite can be further postcured at 650–700° F. (343–371° C.) to optimize the composite properties and increase the $T_g$ to 311° C.

EXAMPLE V 2,3,3',4'-biphenyl tetracarboxylic dianhydride (1.46 g, 5 mmol) and 3,3'-diaminobenzophenone (2.1275 g, 10 mmol), 4-phenylethynylphthalic anhydride (2.4823 g, 10 mmol) were mixed with an additive such as 4-phenylethynyldiphenylmethane (0.5367 g, 2 mmol) or diphenylacetylene as a solid mixture with either ball mill or an efficient mechanical stirrer until it became a homogeneous powder mixture. The solid powder mixture was heated to 232° C. (450° F.) from room temperature in 30 minutes and then held at 450° F. for 1 hour to melt the monomers initially and then reacted with all the monomers to form an imide oligomer. The resulting oligomer resin was then grounded into a solid powder for resin transfer molding (RTM) or resin infusion (RFI) processes and cured at 700° F. (371° C.). The polyimide resin or composite can be further postcured at 650–700° F. (343–371° C.) to optimize the composite properties and increase the $T_g$ to 322° C.

The special feature of this invention is the novel combination of the reactants comprising dianhydrides selected from the group consisting of 2,3,3',4'-biphenyldianhydride (a-BPDA), 2,2',3,3'-biphenyldianhydride, 2,3,3',4'-benzophenone dianhydride (a-BTDA), 3,4'-oxydiphthalic anhydride, 3,4'-methylenedipthalic anhydride, 4,4'-hexafluoroisopropylidene) diphthalic anhydride (HFDA), 4,4'-oxydiphthalic anhydride, and 3,3'-oxydiphthalic anhydride together with the specific group of diamines and the endcaps that can be melt-processed at temperatures between 232–270° C. (450–520° F.), without any solvent. This reaction produces imide oligomers that have low-melt viscosities of 1–60 poise at 260–280° C. The resulting imide oligomers are amenable to RTM, VARTM or resin infusion processes at 260–280° C. to produce high quality polymer composites comprising carbon, glass, quartz or synthetic fiber preforms for use at temperatures ranging from about 550–650° F.

Specifically, a preferred reaction formulation comprises asymmetrical dianhydrides selected from the group consisting of 2,3,3',4'-biphenyldianhydride (a-BPDA), 2,3,3',4'-benzophenone dianhydride (a-BTDA), 3,4'-methylenediphthalic anhydride, and 3,4'-oxydiphthalic anhydride with one or more of the specific diamines and 4-phenylethynylphthalic anhydride (PEPA) or nadic anhydride as the reactive endcap. These compounds can be reacted in the melt to produce imide oligomers that yield a very low viscosity (1–60 poise). This unique melt process, free of solvent, affords a simple manufacturing advantage in term of cost saving by not requiring expensive, high boiling solvents such as N-methyl-2-pyrrolidinone (NMP) to dissolve the monomers in order to produce the oligomers followed by a tedious and costly solvent removal process.

The solvent-free melt-process provides a more consistent quality control in contrast to frequent contamination of high boiling NMP in the final resin product. An example of the solvent-free process is illustrated by the following reaction:

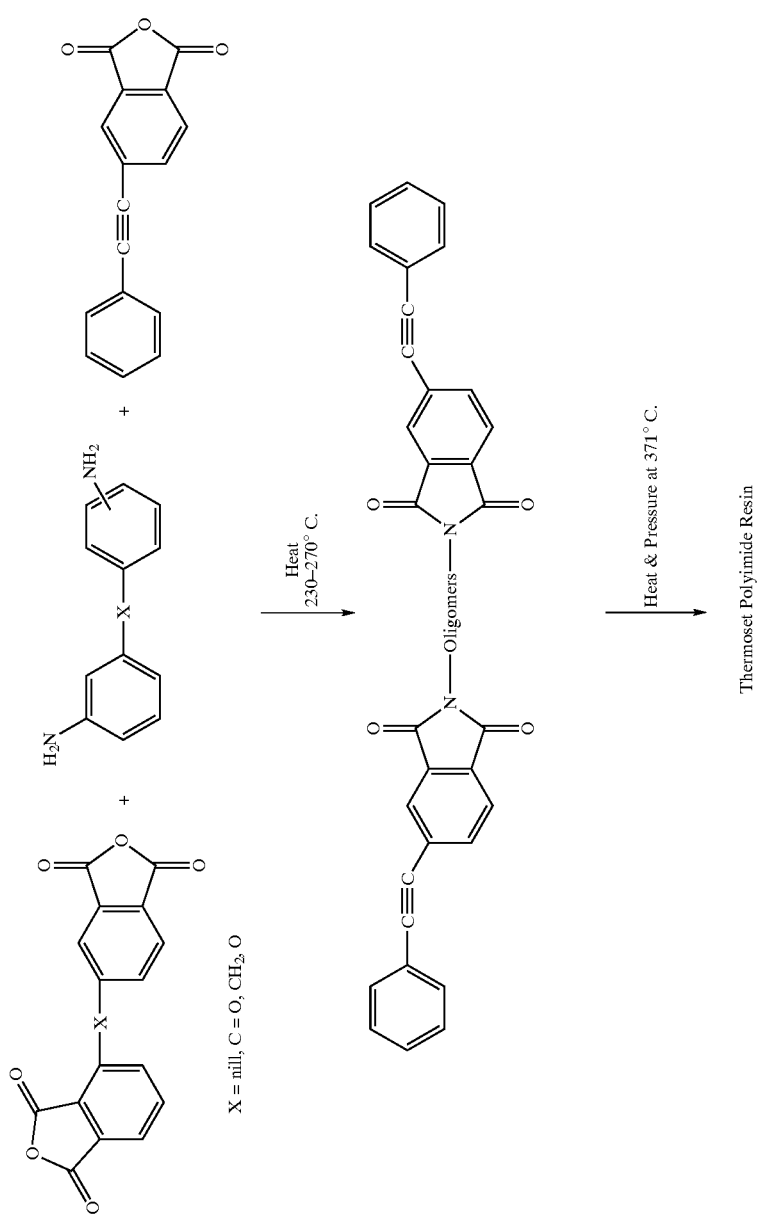

In order to produce imide oligomers of this invention having the low-melt viscosities, the specific aromatic dianhydrides are selected from the group consisting of 2,3,3',4'-biphenyldianhydride (a-BPDA), 2,3,3',4'-benzophenone dianhydride (a-BTDA), 3,4'-methylenediphthalic anhydride, 3,4'-oxydiphthalic anhydride (a-ODPA), 2,2',3,3'-biphenyldianhydride, 4,4'-(hexafluoroisopropy lidene)diphthalic anhydride, 4,4'-oxydiphthalic anhydride, and 3,3'-oxydiphthlic anhydride. The specific diamines are selected from the group consisting of diamines containing two benzene rings; such as 3,4'-diamino diphenylmethane, 3,3'-diaminodiphenyl methane, 3,4-diaminobenzophenone, 3,3'-diaminobenzophenone, 3,4'-oxydianiline 2,2'-diamino biphenyl, 2,2'-dimethylbenzidine, 2,2'-bis(trifluoromethyl) benzidine, and diamines containing three benzene rings with linkages between the benzene rings. The linkage between the benzene rings are the same or different and include $CH_2$, $C_2H_4$, oxygen, nil or $C=O$. The amino group on the first benzene ring can be in the para, meta or ortho positions with respect to the linkage Y between the benzene rings while the second amino group on the second benzene ring is preferred to be in the meta or ortho positions with respect to the linkage. In case of three benzene ring diamines, the third benzene ring can be in para, meta or ortho positions.

The novel feature of this invention is based on the fact that the monomers, namely; the dianhydrides, diamines and the endcaps are melt processable which form imide oligomers at temperatures ranging between 232–280° C. (450–535° F.) without any solvent. Furthermore, the imide oligomers either partially or fully imidized generally have low-melt viscosities in the range of 1–60 poise. These low-melt imide oligomers can be processed easily by resin transfer molding (RTM), vacuum-assisted resin transfer molding (VARTM) or the resin infusion process with preforms including carbon, glass, quartz or synthetic fibers to produce polyimide matrix composites with 288–343° C. (550–650° F.) high temperature performance capability.

While this invention has been described by a number of specific examples, it is obvious that there are other variation and modification that can be made without departing from the spirit and scope of the invention as set forth in the appended claims.

The invention claimed is:

1. Process for preparing low-melt viscosity imide oligomers derived from a solvent-free reaction of stoichiometric effective amounts of at least one asymmetric dianhydride having the formula:

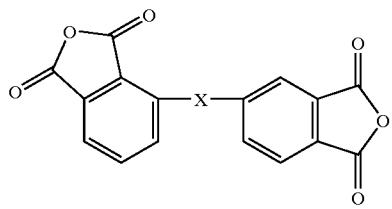

wherein X is selected from the group consisting of nil, $C=O$, $—CH_2$ and oxygen, and at least one aromatic diamine having the formula:

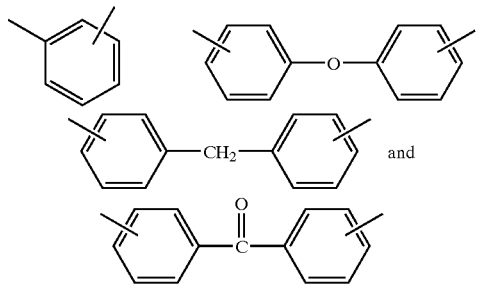

wherein Y is a aromatic radical selected from the group consisting of and an endcap selected from the group consisting of 4-phenylethynylphthalic anhydride and cis-5-norbornene-endo-2,3-dicarboxylic anhydride.

2. The process of claim 1 wherein effective amounts of an additive selected from the group consisting of 4-phenylethynyldiphenyl methane and diphenylacetylene is added to the solvent-free reaction.

3. The solvent-free reaction process of claim 2 wherein the reaction temperature ranges from about 232°–280° C.

4. The solvent-free reaction process of claim 1 wherein at least one of the dianhydrides is

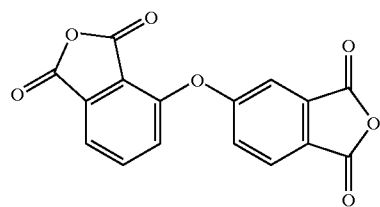

a-ODPA
3, 4'-oxydiphthalic anhydride

5. The solvent-free reaction process of claim 1 wherein at least one of the dianhydrides is

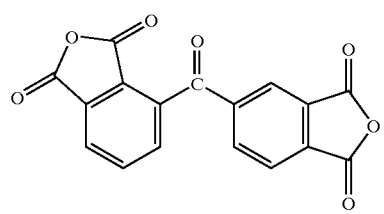

a-BTDA
2, 3,3', 4'-benzophenone dianhydride

6. The solvent-free reaction process of claim 1 wherein at least one of the dianhydrides is

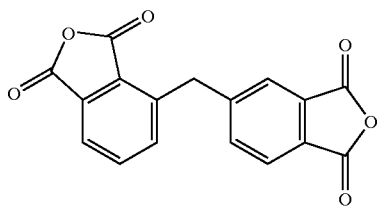

a-MEDA
3,4'-methylenediphthalic anhydride

7. The solvent-free reaction process of claim 1 wherein the Y radical of the diamine has the formula:

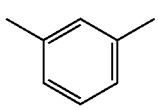

8. The solvent-free reaction process of claim 1 wherein the Y radical of the diamine has the formula:

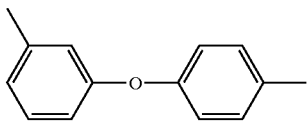

9. The solvent-free reaction process of claim 1 wherein the Y radical of the diamine has the formula:

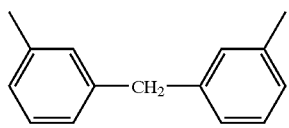

10. The solvent-free reaction process of claim 1 wherein the Y radical of the diamine has the formula:

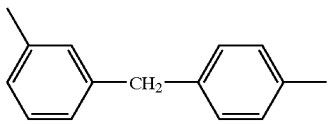

11. The solvent-free reaction process of claim 1 wherein the Y radical of the diamine has the formula:

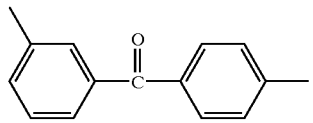

12. The solvent-free reaction process of claim 1 wherein the Y radical of the diamine has the formula:

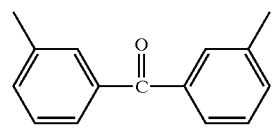

13. The solvent-free reaction process of claim 1 wherein the endcap is 4-phenylethynylphthalic anhydride.

14. The solvent-free reaction process of claim 1 wherein the endcap is cis-5-norbornene-endo-2,3-dicarboxylic anhydride.

15. The solvent-free reaction process of claim 13 wherein the reaction temperatures range from about 232° C. to 280° C. to obtain imidize oligomers having a low-melt viscosity of about 1–60 poises at 260°–280° C., and a cure glass-transition temperature of about 310°–380° C.

16. The thermosetting imidized resins of claim 15 cured with a fiber preform at temperatures ranging from about 650° to 700° F. to obtain thermosetting polyimide matrix-composites having a $T_g$ ranging from about 310°–380° C.

17. The thermosetting polyimide matrix composites of claim 16 wherein the fiber preform is carbon, glass, or a synthetic fiber preform.

18. The imide oligomers obtained by the solvent-free process of claim 1 cured by resin-transfer molding at temperatures ranging from about 650° to 700° F. to obtain thermosetting polyimides having a $T_g$ ranging from about 310°–380° C.

19. Imide oligomers obtained by the solvent-free process of claim 1 cured at temperatures ranging from about 650° to 700° F. to obtain thermosetting polyimides having a $T_g$ ranging from about 310°–380° C.

20. Imide oligomers obtained by the solvent-free process of claim 1.

* * * * *